United States Patent [19]

Tarrson et al.

[11] 4,222,143
[45] Sep. 16, 1980

[54] INTERPROXIMAL BRUSH HANDLE

[75] Inventors: Emanuel B. Tarrson, Chicago; Steven Tisma, Niles; Robert B. Staubitz, Chicago, all of Ill.

[73] Assignee: John O. Butler Company, Chicago, Ill.

[21] Appl. No.: 21,116

[22] Filed: Mar. 16, 1979

[51] Int. Cl.³ .......................... A46B 3/08; A46B 3/18
[52] U.S. Cl. .................................. 15/105; 15/167 R; 15/206; 132/89
[58] Field of Search ................ 15/105, 110, 111, 172, 15/176, 206

[56] References Cited

U.S. PATENT DOCUMENTS

| 1,173,721 | 2/1916 | Hurvitz | 15/206 X |
| 1,996,205 | 4/1935 | Jackson | 15/167 R X |
| 3,559,226 | 2/1971 | Burns | 15/206 X |

FOREIGN PATENT DOCUMENTS 544870 4/1942 United Kingdom ...................... 15/206

Primary Examiner—Edward L. Roberts
Attorney, Agent, or Firm—Laff, Whitesel & Rockman

[57] ABSTRACT

An elongated preferably plastic handle has a sleeve lock on the tip end. When a twisted wire brush is placed in the handle, there is a guy wire effect from the sleeve which holds the brush firmly in place, as the sleeve stretches slightly over a bent end of the twisted wire of the brush. The inventive handle also holds the end of a wooden toothpick, which may be broken without leaving any exposed jagged fibers which could form splinters.

12 Claims, 11 Drawing Figures

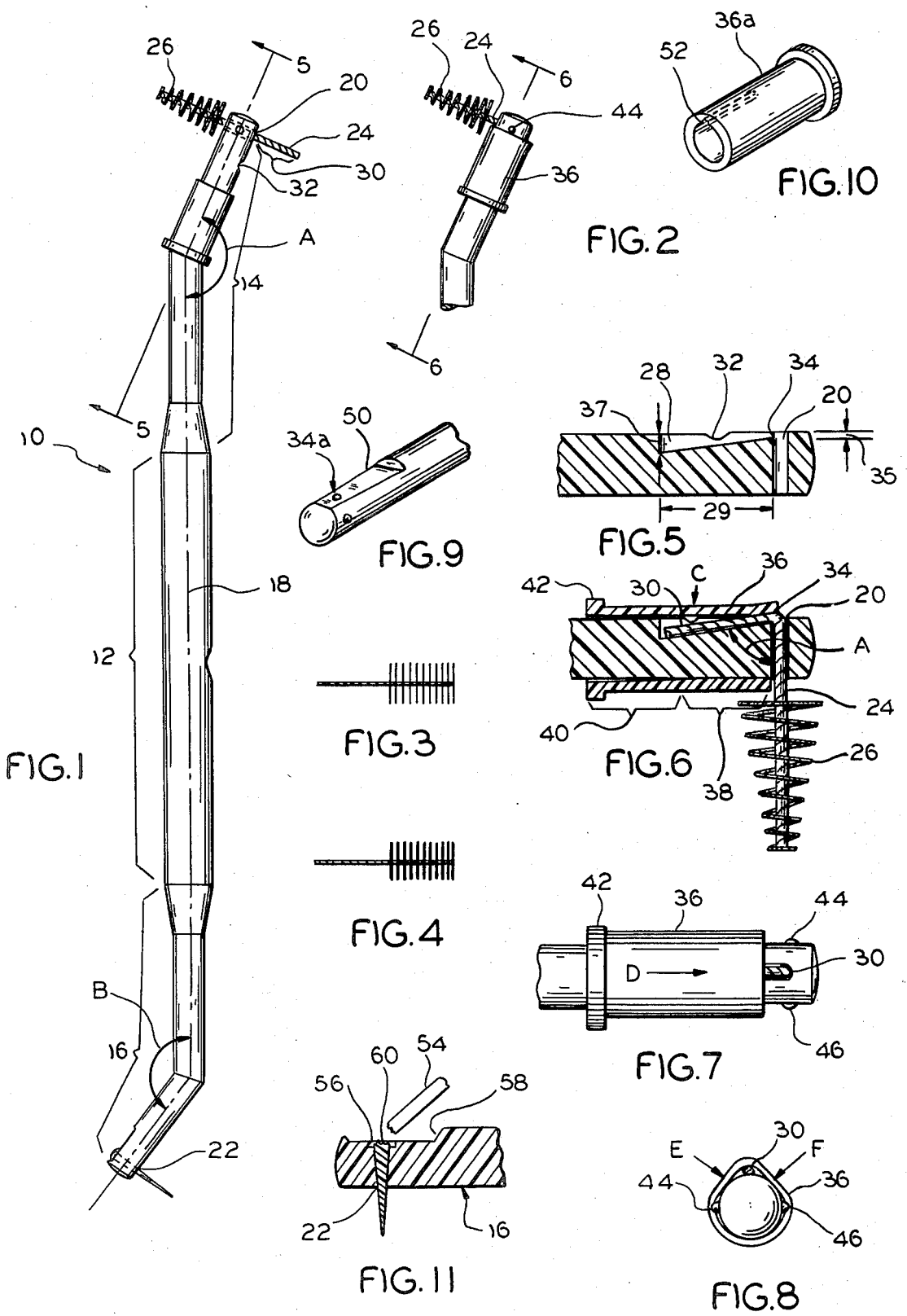

INTERPROXIMAL BRUSH HANDLE

This invention relates to instruments for home dental care and, more particularly, to handles for specialized brushes used to clean the areas of the roots of and the interproximal spaces between human teeth.

To maintain healthy gum tissue, it is highly desirable to provide means for and methods of massaging that tissue. As the massaging occurs, the gum tends to develop a thicker and healthier surface layer upon its tissue for resisting an attack by either disease or mechanical abrasion. However, massaging in these areas presents a number of problems. The teeth are usually closely spaced and (especially at the back of the mouth) the interproximal and root areas between and around the teeth are inaccessible. Therefore, it is difficult to properly stimulate the gums in these noted and other areas.

A number of aids (including various brushes) have been designed for performing this kind of massaging. The brushes should have bristles which rub or wipe perpendicularly across the gum and tooth surfaces, as distinguished from stabbing into them. A brush which is most likely to brush in this manner is a "twisted wire" type wherein bristles are captured between and extended radially from a pair of twisted wires. If the twisted pair of wires must pass through the space between the teeth, it is obvious that their combined diameter cannot be very large. Since they are so small, they are usually made of stainless steel. Even with such strong material, the wires are likely to twist or bend and they may be abrasive enough to damage the gums or enamel.

Accordingly, it becomes necessary to provide a handle which can hold the brush firmly while in use and to hold the twisted wire securely along an extended length thereof. If the brush is to project perpendicularly from the tip of the handle so that it may move sideways to brush into the interproximal areas, it becomes even more difficult to lock the twisted wires in place. Unless so locked, the brush is likely to rotate about the axis of the handle or to bend when it is in use. Thus, it is very important to provide a secure brush grip, in a manner which tends to preclude rotation, bending or bowing of the brush.

This requirement leads to a very expensive type of construction, as compared to the type of construction used for other brushes having somewhat similar usage. For example, the Burns U.S. Pat. No. 3,559,226 shows a metal handle for holding an interproximal brush, with a holding chuck having screw threads, knurling, and the like. The importance which Burns attached to the threaded chuck for holding the brush is immediately apparent from a reading of the claims. Compare the apparent cost for making such a handle with the cost for making a conventional toothbrush, usually a moulded plastic handle which costs a fraction of a cent.

the assignee of this invention has manufactured and sold the brush described in the Burns U.S. Pat. No. 3,559,226 for many years. The high production costs, with a high labor content, were accepted since there was then no satisfactory product without such threaded chuck. However, there were complaints when a customer over-tightened the nut, bent the twisted wires, and ended up with a brush that might have to be discarded before it was used. If they did not tighten the nut sufficiently, the brush was also damaged and often made unusable.

This is unfortunate because a more conventional toothbrush handle structure is made on automatic plastic molding machines which work unattended. For example, it is possible to switch on such a machine and then go home for the night. All night long, the machine is producing parts and no one is present to even observe the machine in operation. With a use of such convention production techniques, the cost of the interproximal handle may also be reduced to a mere fraction of a cent, which is substantially less than the cost of the Burns handle.

Another aid for cleaning the same general root and interproximal area of tooth and gum is a toothpick. For many reasons which are unimportant here, the most satisfactory toothpick is a wooden one. However, it is very difficult to work a toothpick between the teeth, especially at the back of the mouth. Therefore, it is desirable to provide a handle for holding a wooden toothpickprojecting at approximately a right (or other convenient) angle thereto.

If the handle so holds a projecting wooden toothpick, the wood must be severed on the opposite side of the handle so that the unused end of the toothpick does not project from the handle. The easiest way to sever the toothpick is simply to break it. However, then there are likely to be sharp, projecting, broken ends of wood fibers, which may leave splinters in the mouth tissue.

Accordingly, an object of the invention is to provide new and improved handles for interproximal brushes. Here, an object is to provide such handles which may be made at extremely low cost, on unattended automatic machines.

Another object of the invention is to provide an all plastic handle which completely eliminates the need for a screw threaded chuck, while providing a holding capability at least comparable to and preferably greater than the holding capabilities of the chuck. Here, an object is to provide a chuck design which is easily opened and closed so that the brush may be changed very quickly and with almost no effort.

Still another object of the invention is to accomplish these and similar objects in a product which is commercially attractive.

Yet another object is to provide a toothpick holder which may receive and hold the broken end of a wooden toothpick without any danger from splinters at the broken end.

In keeping with an aspect of the invention, these and other objects are accomplished by an all plastic, elongated handle having a smooth and unthreaded sleeve which slides back and forth. A transverse hole pierces the tip end of the handle, the hole having a diameter which is just large enough to easily receive a twisted pair of wires with little, if any, resistance, but is not large enough to permit a significant amount of wiggling movement. Extending from the hole and back along the handle, a downwardly slanting groove is moulded into the plastic. The cross-sectional shape of the sleeve is deformed to produce a guy-wire-like effect which holds the brush in a chuck-like grip.

The opposite end of the handle includes a tapered hole which is countersunk in a recessed area on one side. A wooden toothpick wedges into the tapered hole tightly enough to hold it snugly in place. Then, it is broken by being snapped against an edge of the countersunk region. This leaves any sharp, jagged broken ends of wood fibers below a surface of the handle. This way, they may not leave any splinters in the tissues of the mouth.

A preferred embodiment of the invention is seen in the attached drawing, wherein:

FIG. 1 is a side elevation of the interproximal handle, with a new brush being inserted therein;

FIG. 2 shows the end of the handle with a locking sleeve holding the brush in a chuck-like grip;

FIGS. 3 and 4 show two exemplary alternative forms of twisted wire brushes which may be used with the inventive handle;

FIG. 5 is a side view cross section of the tip end of a first embodiment of the handle showing the principal configuration of a shape which gives the chuck-like action;

FIG. 6 is a cross section similar to that of FIG. 5 showing the interproximal brush locked in place by a sliding sleeve;

FIG. 7 is a top view of the end of FIGS. 5, 6 showing how the movement of the sleeve is arrested in the locking position;

FIG. 8 is an end view of the handle and sleeve showing a guy wire-like effect produced by deformation of the locking sleeve;

FIG. 9 is a perspective view which shows a second embodiment of the tip end of the handle showing a second shape which cooperates with a sleeve to give a chuck-like action;

FIG. 10 is a perspective view which shows a third embodiment wherein the chuck-like action results, at least in part, from a configuration of the sleeve; and FIG. 11 is a cross-section view which shows the toothpick wedged into the holding end of the handle.

The inventive handle (FIG. 1) comprises a generally elongated handle member 10 which has a thickened central region 12, terminated on either end in sections 14,16 of reduced diameter. Each of these end sections 14,16 is bent at an angle A,B of approximately 160 to 150 degrees with respect to the axis 18 of the elongated handle member 10. At each tip end of the handle 10, there is a transverse hole or bore 20,22 extending through the end sections of the handle, the axis of the hole being in the plane including the angles A and B. Preferably, the handle is made from a molded plastic.

The hole or bore 20 has a diameter which is only a very small amount greater than the maximum diameter of a pair of twisted wires 24 (preferably stainless steel) which form the stem and anchored end of the interproximal brush. Therefore, the brush stem formed by these twisted wires slips easily through the hole or bore 20, but it does not wiggle within the hole, in a significant degree.

The hole or bore 22 receives, with a snug fit, an end of a preferably wooden toothpick which fits through the hole with sufficient friction to hold the toothpick in place.

The brush 26 is more or less conventional in its twisted wire construction and it may have any shape which serves interproximal and root brushing needs. For example, the brush 26, shown in FIG. 1, is conical, while FIGS. 3 and 4 show it as being cylindrical. The difference between FIGS. 3 and 4 is that FIG. 3 has relatively thin bristles to make a brush of medium hardness, while FIG. 4 has relatively thick bristles to make a hard brush. These bristles may be either natural or a plastic, preferably nylon. The point is that a separate handle and brush construction, such as this, enables the use of any of a plurality of different kinds of brushes.

The end of the handle tip containing hole or bore 20 is seen in cross section in FIG. 5. There is a thumbnail groove or locking slot 28 which is wide enough to receive the end 30 of twisted wires 24 and long enough to receive a fairly precise length of the twisted wires, which will insure that the brush projects a predetermined distance beyond the other side of the handle when the wire end 30 is bent over and pressed into the thumbnail groove or locking slot 28. In one embodiment, the slot length 29 was approximately 0.330 inches. The slot begins at hole 20, from which the slot bottom slopes downwardly toward an end removed from said bore so that the ends 30 of the twisted wire may be pushed downwardly in direction C, for only a predetermined distance. A depression 32 extends perpendicularly across the slot and receives the edge of a thumbnail.

The instructions to the user may suggest either of two ways to go about locking the brush in place. First, the user may bend the free end 30 of the twisted wire 24 upwardly, as viewed in FIG. 1. This forms the twisted wire to have a substantially right angle bend over the tip end. The bent end 30 (FIG. 6) is then rotated to fit down and into the slot 28. Second, the user may bend the free end 30 of the twisted wire 24 downwardly, as viewed in FIG. 1. The end 30 fits into the slot 28 (FIG. 6) and is pushed downwardly by the thumbnail pressed into the depression 32. Either way, the free end 30 of the twisted wire rests in the thumbnail slot 28, as best seen in FIG. 6.

The slot 28 begins at a shoulder 34 which is recessed below the surface of the handle by a distance which is, roughly speaking, about equal to the radius of the twisted pair of wires. In one embodiment, a pair of twisted wires 24 had a diameter in the range of 0.028–0.08 of an inch in diameter. The shoulder 34 was recessed at 35 about 0.018 of an inch below the surface of the handle. The distant end 37 of slot 28 had a depth of approximately 0.060 of an inch, in this embodiment.

Thus, the twisted wire pair 24 projects above the surface of the handle and forms an obstruction there, in order to limit the forward sleeve travel and to deform the sleeve to produce a guy-wire-like effect.

A sleeve 36 is shaped and proportioned to slide back over the reduced diameter end section 14 of the handle far enough to expose all of the thumbnail groove 28 or forward far enough to lock the brush in place. The interior of the sleeve has a contour which is cylindrical throughout a first length 38 nearest the hole 20. The contour is slightly tapered throughout a second length 40 to assist in slipping the sleeve over the end of the handle, at the time of manufacture. The sleeve 36 terminates in a ridge 42 which assists in holding and moving it.

The tip end (FIG. 7) of the handle 10 includes two oppositely disposed projections 44,46. Preferably, the sleeve 36 may be forced over these projections and on to the handle, but it will not fall off the handle unless pulled with a substantial force. In part, this is because the taper of section 40 acts as a guide for slipping over the projections 44,46, but the conical section 38 tends to abut the projections and this prevents removal of the sleeve.

After the brush is in place and the end 30 of twisted wires 24 has been bent over, the sleeve 36 is forced as far as it will go in direction D. Not only the projections 44,46 but also the hump formed by the twisted wires 24 bending over the shoulder 34 form obstructions which limit the outward sleeve movement and prevent its removal from the end of the handle. Moreover, as seen in FIG. 8, the sleeve tends to be distorted in cross section to provide a bracing effect which is somewhat similar to the bracing of guy wires, thereby forming a very tight binding.

The assignee of this invention encountered problems with the handle shown in the Burns U.S. Pat. No. 3,559,226 because when his nut 19 was over-tightened, his twisted wires 16 deformed and crimped to cause the brush to move into a position somewhat parallel to the handle at the end 12. After the crimp formed in the twisted wire, it was difficult to correctly lock the brush in its preferred position. Sometimes, a particularly determined person could even force the nut 19 off the end of the handle, with the brush in place. This is not possible with the present invention owing to the obstruction of the twisted wire above shoulder 34.

The guy wire effect caused by the deformation of the end of sleeve 36 is seen at E,F in FIG. 8. The tension in sleeve 36 helps secure the end 30 and thus the brush in place even more tightly, it is thought, than was possible with only the nut 19 of the Burns' patent.

A firm anchoring of the twisted wires 24 wrapping over the shoulder 34 helps to stabilize the brush when locked in position.

The embodiment of FIG. 9 is slightly different from the embodiment of FIG. 5 since a flat portion 50 replaces the thumbnail slot 28. The flat portion tapers from shoulder 34a in the same manner that the slot 28 tapers from shoulder 34. Also, the taper forms a locking shoulder at 34a, to prevent the sleeve from being pushed off the end, in the same manner that shoulder 34 is formed in the embodiment of FIG. 5 to prevent the sleeve from being pushed off the end. The principal difference is that there is no need to fit the end 30 of the twisted wire 24 into slot 28. Therefore, some people (especially those with an impairment of finger action) may find it easier to use a brush handle in the form of FIG. 9, as compared to the handle of FIGS. 5 and 6.

The embodiment of FIG. 10 does not necessarily require any slot 28 or other depression in the handle, although it may be used in connection with either. Rather, the sleeve 36a is molded with an inner recess 52 for receiving the end 30 of the twisted wire 24. The sleeve must be indexed so that the recess 52 will fit over the end 30 of the twisted wire 24. There is an action squeezing the recess walls against the twisted wire as the sleeve deforms, as shown in FIG. 8. This action tends to grip the end 30. Another consideration is the need to index the sleeve, which may be awkward for some people.

FIG. 11 shows how the toothpick is fitted into and held by the bore 22, at the opposite end 16 of the handle 10. The bore 22 is generally tapered so that a tapered end of a conventional round wooden toothpick 54 may be forced therein and held with a firm friction fit. The upper end (as viewed in FIG. 11) of the bore 22 is countersunk at 56, within a clearance space 58. This space is provided to enable the toothpick 54 to swing far enough to snap and break when a suitable force is applied to the toothpick, perpendicularly to the axis of bore 22.

As the toothpick is snapped off, the breaking force is applied against the rim of the bore 22 in the bottom of the countersunk recess 56. Hence, the jagged ends 60 of broken wood fibers are contained within the confines of the countersunk recess 56. This means that no splinters are exposed to catch in the tissues of the mouth.

Those who are skilled in the art will readily perceive how the inventive structure may be modified, without departing from the scope and the spirit of the invention.

We claim:

1. An elongated interproximal brush handle having a transverse bore near at least one tip end thereof, the diameter of said bore being slightly greater than the diameter of a twisted pair of wires of a twisted wire brush, a locking area formed in said handle and extending away from said transverse bore, the area beginning at a shoulder and thereafter sloping downwardly to an end removed from said bore, said shoulder being formed to a depth in said handle which exposes said twisted wire above the surface level of the handle, the depth of the area end removed from said bore being low enough to enable an end of said twisted wire to be bent over said shoulder and pressed below the surface level of said handle, and a sleeve for sliding over said end of said twisted wire to come to rest against the twisted wire which is exposed above said surface of said handle where the wire is bent over said shoulder.

2. The handle of claim 1 wherein said locking area is a slot for receiving the end of said twisted wire.

3. The handle of claim 1 wherein said locking area is flat portion on said handle, said flat portion extending from said shoulder to said removed end.

4. The handle of claim 1 wherein said sleeve has a recess formed therein for receiving said twisted wire bent over said shoulder.

5. The handle of claim 1 wherein said sleeve has a internal contour which is cylindrical on one end which is near said bore and tapered on the other end which is removed from said bore.

6. The handle of claim 5 wherein said cylindrical end of said sleeve is deformed when pushed over the exposed twisted wire above said shoulder, thereby producing a guy wire effect upon said twisted wire.

7. The handle of claim 6 and projections on said tip end in the vicinity of the twisted wire exposed above said shoulder, said projections extending outwardly from said handle far enough to restrain said sleeve but not far enough to prevent said sleeve from being forced over said projections except when said sleeve is deformed over said twisted wire.

8. The handle of claim 1 wherein there is a tapered transverse bore near a tip at the opposite end of said handle, said tapered bore terminating in a countersunk recess which is deep enough to contain any broken ends of wood fibers which may appear when a wooden toothpick is forced through said tapered hole and then snapped off.

9. The handle of claim 8 and a clearance area formed around said countersunk recess to enable said toothpick to be snapped against the rim of the tapered bore at the bottom of countersunk region.

10. An elongated plastic handle having parallel transverse bores at opposite ends thereof, said handle being bent in the plane defined by the axes of the parallel bores, a sliding sleeve fitting over one of the ends of said handle to slide toward and away from the bore in said one end, a slot in said handle beginning at the bore in said one end and extending away from the bore in said one end through at least a part of the area where the sleeve slides, said slot being shallow enough on the end next to said bore for receiving only a lower portion of a pair of twisted wires whereby said sleeve cannot pass over said twisted pair of wires and being deep enough on the end displaced from said bore for enabling said pair of twisted wires to pass beneath said sleeve.

11. The handle of claim 10 and a depression extending perpendicularly across the slot for receiving the edge of a thumbnail pressing the end of said pair of twisted wires into the slot, the depth of said depression limiting the depth to which the end of said twisted pair of wires may be pressed into said slot.

12. The handle of claim 10 wherein the bore on the opposite end is tapered, a recessed area countersunk at the large end of said taper, and a relief area containing said countersunk recessed area.

* * * * *